US011422107B2

(12) United States Patent
Aas et al.

(10) Patent No.: US 11,422,107 B2
(45) Date of Patent: Aug. 23, 2022

(54) SYSTEM AND METHOD FOR ESTIMATING A TEMPERATURE OF A LIQUID SAMPLE

(71) Applicant: RADIOMETER MEDICAL APS, Brønshøj (DK)

(72) Inventors: Flemming Aas, Dyssegaard (DK); Peter Frischauf, Brøndby (DK); Erik Hellleso Nicolajsen, Copenhagen (DK)

(73) Assignee: Radiometer Medical ApS, Bronshoj (DK)

( * ) Notice: Subject to any disclaimer, the term of this patent is extended or adjusted under 35 U.S.C. 154(b) by 441 days.

(21) Appl. No.: 16/466,419

(22) PCT Filed: Nov. 30, 2017

(86) PCT No.: PCT/EP2017/080906
§ 371 (c)(1),
(2) Date: Jun. 4, 2019

(87) PCT Pub. No.: WO2018/104134
PCT Pub. Date: Jun. 14, 2018

(65) Prior Publication Data
US 2019/0346398 A1    Nov. 14, 2019

(30) Foreign Application Priority Data
Dec. 7, 2016   (DK) .......................... PA 2016 00746

(51) Int. Cl.
G01N 27/327   (2006.01)
G01N 33/49    (2006.01)
(52) U.S. Cl.
CPC ......... *G01N 27/3274* (2013.01); *G01N 33/49* (2013.01); *G01N 33/4925* (2013.01)

(58) Field of Classification Search
CPC ............... G01N 27/3274; G01N 33/49; G01N 33/4915; G01N 33/4925; Y10T 436/204998; Y10T 436/2575
(Continued)

(56) References Cited

U.S. PATENT DOCUMENTS 4,115,230 A     9/1978  Beckman
4,415,534 A *  11/1983  Lundsgaard ........... G01N 35/00
                                                        422/138
(Continued)

FOREIGN PATENT DOCUMENTS

CN        1795369 A      6/2006
CN      100998507 A      7/2007
(Continued)

OTHER PUBLICATIONS

International Search Report for International Application No. PCT/EP2017/080906, dated Feb. 15, 2018 (three pages).
(Continued)

*Primary Examiner* — Maureen Wallenhorst
(74) *Attorney, Agent, or Firm* — Finnegan, Henderson, Farabow, Garrett & Dunner, LLP

(57) ABSTRACT

The disclosure relates to an apparatus for the analysis of biological liquid samples, the apparatus having a measurement chamber defining a sample volume with an inlet and an outlet; a fluid handling system adapted for feeding a liquid to the sample volume through the inlet and for removing the liquid through the outlet; a thermostatic sample heater device adapted for controlling a sample temperature of a liquid sample in the measurement chamber; and a processor unit. An analyte sensor output may be corrected on the basis of the initial temperature thus determined. A corresponding method for the analysis of biological liquid samples is provided. Furthermore, a method of performing a quality
(Continued)

control procedure using the apparatus or the method is disclosed.

20 Claims, 3 Drawing Sheets

(58) Field of Classification Search
USPC .......... 436/63, 68, 133, 147, 180; 422/82.12
See application file for complete search history.

(56) References Cited

U.S. PATENT DOCUMENTS

| | | | |
|---|---|---|---|
| 5,482,372 A * | 1/1996 | Bataillard | G01N 25/42 |
| | | | 374/148 |
| 6,114,176 A | 9/2000 | Edgson et al. | |
| 6,123,827 A | 9/2000 | Wong et al. | |
| 6,908,224 B2 | 6/2005 | Schneider et al. | |
| 8,728,288 B2 * | 5/2014 | Aas | G01N 33/4915 |
| | | | 204/411 |
| 9,501,070 B2 * | 11/2016 | Higginbotham | B01L 7/52 |
| 2003/0042181 A1 | 3/2003 | Metzner | |
| 2003/0225341 A1 * | 12/2003 | Ruether | G01N 33/4925 |
| | | | 600/549 |
| 2007/0174016 A1 | 7/2007 | Ding et al. | |
| 2012/0329082 A1 | 12/2012 | Viola et al. | |
| 2014/0116128 A1 | 5/2014 | Mantinband et al. | |
| 2014/0273187 A1 | 9/2014 | Johnson et al. | |
| 2016/0033340 A1 | 2/2016 | Todd et al. | |

FOREIGN PATENT DOCUMENTS

| | | |
|---|---|---|
| CN | 101087997 A | 12/2007 |
| CN | 101311684 A | 11/2008 |
| CN | 102271582 A | 12/2011 |
| EP | 1 558 921 B1 | 8/2005 |
| GB | 2508358 A | 6/2014 |
| JP | 2000-509817 | 8/2000 |
| JP | 2006-504936 | 2/2006 |
| JP | 2009-074872 | 4/2009 |
| JP | 2016-512339 | 4/2016 |
| JP | 2016-519605 | 7/2016 |
| WO | WO 98/32013 | 7/1998 |
| WO | WO 01/089692 A2 | 11/2001 |
| WO | WO 2005/113819 A2 | 12/2005 |

OTHER PUBLICATIONS

Written Opinion of the International Searching Authority of International Application No. PCT/EP2017/080906 (six pages).

* cited by examiner

SYSTEM AND METHOD FOR ESTIMATING A TEMPERATURE OF A LIQUID SAMPLE

This application is a national stage filing under 35 U.S.C. § 371 of International Application No. PCT/EP2017/080906, filed on Nov. 30, 2017, which claims priority to Danish Patent Application No. PA 2016 00746, filed Dec. 7, 2016. The contents of these applications are each incorporated herein by reference.

The present invention relates in one aspect to a system and method for estimating a temperature of a liquid sample. More particular, the present invention relates in one aspect to an apparatus and method for estimating a temperature in an apparatus for the analysis of biological liquid samples. In a further aspect, the invention relates to an apparatus and a method for correcting an analyte sensor output based on the estimated temperature. In a yet further aspect, the invention relates to a method of performing a quality control measurement in an apparatus for the analysis of biological liquid samples, in particular a method of performing a quality control measurement in respect of $pCO_2$.

BACKGROUND OF THE INVENTION

Measurement equipment for medical analytics is designed to measure on biological samples to determine the presence and quantity of certain analytes in the biological sample. The measurements are often performed in the course of a diagnostic process before, during, and/or after a treatment of a pathological state of a patient. The precision of these measurements is often crucial for the correct diagnosis of the pathological state of the patient, and the reliability of a timely and precise result can be life-critical. The reliability and precision of such medical measurement equipment is therefore typically subject to strict quality procedures, which typically impose very rigorous requirements for the laboratory set-up and the conditions to be maintained in the laboratory in order to reliably achieve the required precision. The quality and correctness of the measurements obtained is constantly checked using quality control (QC) procedures by measuring on standardized quality control solutions under the same conditions as for actual samples. Any deviations beyond specified QC tolerance ranges are assessed and are either dealt with in a correction to comply, or may result in a service warning or stop. The QC tolerances may be specified by the manufacturer guaranteeing a certain measurement precision, and/or may be subject to regulatory provisions. An example for a particularly useful, yet stringent set of regulations, is the guideline for the quality control of laboratory-medical analyses issued by the German association of medical doctors ("Richtlinie der Bundesärztekammer zur Qualitätssicherung Laboratoriums-medizinischer Untersuchungen—Rili-BÄK") as of 25 Sep. 2014.

Blood analysis devices and apparatus play an important role in medical diagnostics. Obtaining results with the highest possible precision from blood analysis apparatus is therefore of the utmost importance to the users and is a constant quest for the producers of such blood analysis equipment. However, an increasing demand for rapid access to such medical analytics in life-critical situations and at the point of care makes it virtually impossible to comply with requirements that are usually designed for a set-up in a controlled laboratory specialized in medical analytics. Violating the specifications for the set-up may jeopardize the reliability and precision of the results as e.g. required by the above-mentioned quality control regulations, and may, in the worst case, put patient safety at risk.

One of the environmental parameters to be regarded in this respect is the actual temperature of the apparatus, which is determined by the actual temperature of the room in which the apparatus is located, the potential exposure to localized heating and/or cooling sources, such as incident solar radiation, draft from an open window, or the inappropriate dissipation of heat generated by the operation of the apparatus itself. This may, for example, affect the temperature of the reservoirs of QC-solutions. Furthermore, certain QC-solutions are stored refrigerated prior to use, and the actual temperature upon installation of a new QC-solution pack may therefore deviate from the temperature range that is otherwise required for obtaining QC-measurement results that are compliant with applicable regulations. Installing a new QC-solution reservoir taken directly from the storage cooler may therefore set back the instrument's readiness for measurement until the QC-solution pack has attained the appropriate temperature.

As mentioned above, the QC-procedures involve measuring the QC-solutions under the same conditions as actual samples of body fluids, such as blood. This includes measuring within the same time frame for filling and performing the analysis as for these biological liquid samples. It further includes performing the QC-measurements on the QC-solutions at the same target temperature as for the biological liquid samples. Typically, the target temperature is in the range between 36° C. and 38° C., preferably 37° C., whereas the QC-solution is at temperatures well below the target temperature, such as at the temperature of the room where the apparatus is located, or otherwise at lower temperatures as discussed above. When performing a QC-measurement, a sample of QC solution is prepared for measurement in a measurement chamber by injecting an amount of the relevant QC-solution into the measurement chamber and heating it to the target temperature. However, in apparatus designed for fast measurement cycles that provides an analytical result on a biological liquid sample within the range of minutes or below, the resulting short time for heating the sample may pose a challenge to establishing a correct equilibrium of the QC-solution at the target temperature. Determining the initial temperature of the QC-solution upon injection is therefore important to assess the validity of the QC-procedure.

In one approach, a user may be required to key in the temperature of the QC-solution used for a QC-measurement, either each time the QC-procedure is performed, or e.g. as a default value. However, such an approach is tedious for the user, and susceptible to human error.

In another approach, it is conceivable to equip each QC-solution pack with a temperature reading device, which may further log temperature data, and provide temperature data to a processor unit of the analytic apparatus. However, this would add to the cost of each of the QC-solution packs, which are frequently replaced, and may thus be an expensive approach, at least in terms of the perpetual cost for running the analytic apparatus.

In a yet further approach, it may be conceived to measure the temperature of each QC-solution by installing a respective temperature sensor in an automatic fluid handling system of the analytical apparatus, e.g. at each of the respective ports for connecting the QC-solution packs to the fluid handling system of the apparatus. However, such a solution has the disadvantage that it requires modification of the hardware of the apparatus, and is therefore not easily retro-fitted to an existing apparatus.

At least for these reasons there is a need for an inexpensive, yet reliable and precise, method and system for determining the initial temperature of a liquid injected into a measurement chamber of an apparatus for the analysis of biological liquid samples. Furthermore, there is a need for an improved method and system for assessing the validity of measurements performed in an apparatus for the analysis of biological liquid samples. More particularly, there is a need for an improved method and system for assessing the validity of quality control (QC) measurements performed in an apparatus for the analysis of biological liquid samples using calibrated QC-reference liquids.

SUMMARY OF THE INVENTION

In one aspect, the object of the present invention is to provide a system and/or a corresponding method for determining an initial temperature of a liquid injected into a measurement chamber of an apparatus for the analysis of biological liquid samples overcoming at least some of the above-mentioned disadvantages, or to provide an alternative.

In a further aspect, the object of the present invention is to provide a system and/or a corresponding method for assessing the validity of measurements performed in an apparatus for the analysis of biological liquid samples overcoming at least some of the above-mentioned disadvantages, or to provide an alternative.

In a yet further aspect, the object of the present invention is to provide an improved system and/or a corresponding method for assessing the validity of quality control (QC) measurements performed in an apparatus for the analysis of biological liquid samples using calibrated QC-reference liquids.

The objects are at least partly attained by the appended claims, wherein advantageous embodiments are disclosed in the dependent claims and the description below.

According to a first aspect, an apparatus for the analysis of biological liquid samples is provided, the apparatus comprising: a measurement chamber defining a sample volume with an inlet and an outlet; a fluid handling system adapted for feeding a liquid sample to the sample volume through the inlet and for removing the liquid sample through the outlet; a thermostatic sample heater device adapted for controlling a sample temperature of the liquid sample in the measurement chamber; and a processor unit; wherein the processor unit is configured for determining an initial temperature of the liquid sample injected into the measurement chamber based on fluid flow data from the fluid handling system and sample heating data from the sample heater device.

Under operation, the fluid handling system injects a liquid through the inlet into the measurement chamber at a controlled flow. The injected liquid has an initial temperature below a target temperature for liquid samples to be analysed in the measurement chamber. The thermostatic sample heater is programmed to control the sample temperature to a target temperature above the temperature of the injected liquid.

Bioanalytical measurements on body fluids, such as blood, are typically performed at temperatures corresponding to a body temperature. For bioanalytical applications the target temperature is therefore typically set to a value between 36° C. and 38° C., preferably 37° C., whereas the injected liquid typically has a lower temperature, e.g. the temperature of the surroundings of the apparatus, i.e. room temperature. The thermostatic sample heater therefore applies heat in order to warm the injected liquid up to the target temperature. The thermostatic sample heater applies heat to the liquid sample upon injection, i.e. immediately or very soon after the liquid sample has entered the measurement chamber through the inlet. Typically, the thermostatic sample heater is operated during injection, i.e. at the same time as the fluid handling is operated to inject the liquid sample into the measurement chamber, and heat is therefore applied by the thermostatic sample heater to the liquid sample as soon as the liquid sample enters the measurement chamber through the inlet port. Thereby, a rapid conditioning of the liquid sample to the target temperature is achieved, where analysis measurements can be performed. This allows for shortening the measurement cycle and provides the user with fast analysis results on the biological liquid samples to be analysed. Corresponding quality control measurements are then also performed under the same conditions and with the same timing, including the timing of the sample heating process.

Advantageously, the thermostatic sample heater device is operated at least for pre-heating the liquid sample to target temperature prior to starting actual analysis measurements on the liquid sample. Operation of the sample heater as a pre-heater device is particularly advantageous in a set-up where the measurement chamber is encapsulated in a controlled thermal environment, such as a thermostatically controlled housing defining a fixed temperature around the measurement chamber, wherein most preferably the fixed temperature corresponds to the target temperature.

Preferably, the processor unit is adapted to receive fluid flow data from the fluid handling system and sample heating data from the sample heater device. Typically, the processor unit is programmed to retrieve data characterizing the injection flow and the heating applied to the injected liquid, and determines the initial temperature of the injected liquid. Since the sample heater is a thermostatic heater controlling the sample temperature to a fixed target temperature, the flow and heater data are sufficient to determine the initial temperature. For a fixed target temperature, an initial temperature value may, for example, be determined using a calibration that has been established beforehand for a given type of apparatus, and/or for each specific apparatus, and which is stored in the processor, e.g. in the form of a formula, such as a polynomial curve or a linear function, or in the form of a look-up table.

Thereby, a simple and efficient way of directly determining the initial temperature of the injected liquid sample from calorimetric considerations is provided, without the need of installing and maintaining additional temperature sensors in the apparatus. The temperature determination can therefore also be easily retro-fitted to existing bio-analytic apparatus equipped with a fluid handling system for controlling the filling of the measurement chamber and a thermostatic sample heater for controlling the sample temperature to a fixed target temperature. For example, a retro-fit may in some cases even be achieved by software update that ensures that the processor unit retrieves the required fluid flow and sample heater data, and contains the required conversion curve for determining the initial temperature based on the fluid flow and sample heater data.

Advantageously according to some embodiments, the initial temperature is determined from a calibration formula as a function of parameters representative of the injection flow and of the heating applied by the thermostatic sample heater to the injected liquid. Preferably, the calibration formula is programmed or tabulated in the processor unit. Advantageously, the calibration formula is determined beforehand by calibration of the apparatus by injecting fluid at different known initial temperatures. Further advantageously, the calibration formula is a polynomial, preferably a linear function. Advantageously, the coefficients of the polynomial or linear function may be determined from the calibration data by means of a fitting routine, such as a least-square-fit.

A calibration formula based on sample flow and heating data may assume remaining parameters or conditions as a constant, which otherwise might enter into the calorimetric considerations. The term constant is here to be understood as constant to within significant error limits, i.e. variations of these parameters or conditions are considered as insignificant for the desired/relevant precision of the initial temperature determined, or these parameters/conditions are explicitly or implicitly kept constant for a given calibration. For example, the exact calorimetric configuration including e.g. the thermal environment and properties of the measurement chamber, may explicitly or implicitly be included in the calibration formula that has been established beforehand for a given type of apparatus, and/or for each specific apparatus.

For example, a certain target temperature setting may be explicitly accounted for by choosing a different pre-stored calibration curve depending on the target temperature setting. A calibration formula for a given type of apparatus implicitly contains effects of e.g. thermal and calorimetric characteristics of a given measurement chamber and apparatus design on the result of determining the initial temperature. Influences of component variations, e.g. due to production tolerances for nominally identical implementations of the apparatus or parts thereof may either be ignored as insignificant, or, if considered significant, taken into account as simple corrections to the general, apparatus type-specific calibration, since such component related variations may be considered as systematic deviations. An example for such component variations is discussed in more detail with respect to electrical heating elements further below.

Typically the same type of liquid is used for calibration as later on in the analysis or QC-measurements for which the initial temperature is to be determined. Nevertheless, a further error might be introduced, if the liquid sample for which the initial temperature is to be determined is different from the liquid for which the calibration formula has been established, e.g. due to different heat capacities for different liquids. In so far differences in heat capacity are considered significant, this may e.g. be taken into account by providing corresponding calibration curves for different types of liquid depending on the sample liquid injected. Typically, however, the liquid samples of concern here can be considered as aqueous solutions having essentially the same heat capacities.

The initial temperature may also be determined in the case, where it might be desirable to select a different target temperature for different samples. In this case, the respective calibration curves may be prepared beforehand for a set of fixed target temperatures of the thermostatic sample heater device covering the intended target temperature operation range and stored in the processor unit. The processor unit will in this case be programmed to include the target temperature setting in the data to be retrieved and select the appropriate calibration curve accordingly.

The apparatus for the analysis of biological liquid samples, i.e. samples of body fluids, such as blood samples, is for use at a point of care. Therefore compliance with a specific, well controlled temperature of the surroundings of the apparatus cannot be relied upon. As mentioned above, liquids, such as QC-solutions are often injected into the measurement chamber from a reservoir that is at thermal equilibrium at room temperature. Determining the actual initial temperature of the solution when it is injected into the measurement chamber is therefore most useful for the correct and precise operation of the bioanalytical apparatus. The present invention, which allows for a simple and efficient assessment of the initial temperature of the injected liquid, thus also facilitates the use of the apparatus in an environment, such as at a point of care, which is less controlled than a set-up in a specialised bio-analytic laboratory.

Advantageously according to some embodiments, the fluid flow data comprises a parameter representative of the flow rate of the liquid injected to the sample volume, and the sample heating data comprises a parameter representative of the heating power applied by the thermostatic sample heater device to establish a target temperature in the sample volume under steady flow conditions. This allows for a precise and instantaneous derivation of the initial temperature already during the procedure of filling the measurement chamber with a liquid sample to be measured.

Advantageously according to some embodiments, the fluid handling system comprises a positive displacement pump, such as a peristaltic pump. The fluid handling system is configured for feeding (or 'injecting' as phrased above) a fluid to the measurement chamber through the inlet at a controlled flow rate and/or amount. The fluid handling system may further be configured for determining a flow rate and/or an amount of liquid fed to the measurement chamber through the inlet. Injection may be brought about by a pump, such as a positive displacement pump, and may e.g. be implemented as a suction applied by means of the pump arranged downstream of the measurement chamber, i.e. on the outlet side. Typically, positive displacement pump, such as a peristaltic pump is employed. This allows for establishing a well-controlled flow rate of the injection flow by directly setting pump operational parameters, which control the displacement. Thereby it is achieved that the flow data may simply be derived directly from a pump operational parameter setting.

As mentioned above, the thermostatic sample heater device is for controlling, i.e. regulating a sample temperature of a liquid sample in the measurement chamber according to a target temperature setting. Thereby, a rapid conditioning of the liquid sample to the target temperature is achieved, where analysis measurements can be performed. Preferably according to some embodiments, the thermostatic sample heater device comprises a temperature sensor element, in thermal contact with the sample volume, such as a thermistor arranged inside the measurement chamber. Preferably, the temperature sensor element is located at a central location inside the measurement chamber between the inlet and the outlet, such as at equal flow distance from both the inlet and the outlet. Thereby a reliable temperature reading representative of the temperature of the liquid sample is achieved.

Further advantageously, the thermostatic sample heater device comprises an electric heating element, such as a resistive heating element. Most preferably, the electric heating element, such as a resistive heating element, is physically attached to or integrated with the walls of the measurement chamber. Thereby, a rapid, reliable, and reproducible conditioning of the liquid sample to the target temperature is achieved, where analysis measurements can be performed. By physically attaching or integrating at least one electric heating element with the walls of the measurement chamber it is achieved to provide a good thermal transfer between the heating element and the liquid sample inside the measurement chamber to ensure a rapid and reproducible transfer of heating energy from the heating element to the liquid sample. While thermal losses are unavoidable, the particular choice of physical attachment or integration of the electric heating element, in particular a resistive heater, with the measurement chamber walls provides a well-controlled heating mechanism, where the heat transferred to the sample is systematically linked to the heat generated by the heating element, and further to the power/energy consumed by the heating element. The skilled person is further instructed to optimize the specific arrangement of the physical attachment or integration of the electric heating element for efficient, rapid and/or reproducible heat transfer to the liquid sample within particular design constraints of a specific measurement chamber set-up.

The arrangement of an electric heating element in physical attachment or integration with the measurement chamber is particularly synergistic in combination with a measurement chamber designed for very small sample volumes allowing for rapid conditioning of a liquid sample and for rapid completion of a measurement cycle on the liquid sample. For example, a measurement chamber may be made in a planar sandwich construction of two counter-stacked ceramic substrates/plates separated by a polymer spacer gasket with a recess defining a sample volume. The sample volume may have cross-sectional dimensions in the millimetre and sub-millimetre range. A sensor assembly having a measurement chamber with a sandwich construction is, for example, disclosed in U.S. Pat. No. 8,728,288 B2, which is hereby included by reference. Advantageously, an electric heating element may be printed directly on the backside of at least one of the ceramic substrates/plates forming the top and bottom walls of the measurement chamber. Alternatively or in addition thereto, it is conceivable to place an electric heating element on at least one of the inside surfaces of the measurement chamber, e.g. printed on a surface in direct contact with the sample volume. Thereby, a highly responsive device allowing for an immediate and direct temperature control of the liquid in the sample volume is achieved. Power may be supplied to the electric heating element by any suitable means, preferably by supplying DC or AC current to the electric heating element through electrically conducting leads. However, it is also conceivable to supply power to the electric heating element through an inductive coupling.

It may be noted, as mentioned above, that component variations, if considered significant, may be taken into account as specific corrections to the general, type-level apparatus calibration. For example, variations in the resistance from one resistive heating element to another may arise. Such component variations may lead to a variation in the factor of heat generated by a specific resistive heating element and transferred to the liquid sample inside the associated measurement chamber. This may e.g. be relevant if a measurement chamber with integrated heating element is replaced. Such component variations may, however, easily be taken into account by a corresponding specific correction factor to the type-level calibration provided by the manufacturer of the apparatus. The specific correction factor may also be provided, for example, by the manufacturer of the apparatus in relation to a resistance specification of the resistive heating element.

Advantageously according to some embodiments, a target temperature in the sample volume is in the range between 35° C. and 39° C., or between 36° C. and 38° C., and preferably 37° C.

Advantageously, the apparatus comprises an isothermal encapsulation of the measurement chamber, wherein the isothermal encapsulation encloses the measurement chamber like a housing with thermally controlled and/or thermally regulated inner surfaces. Preferably, the temperature of the inner surfaces of the isothermal encapsulation is controlled and/or regulated to a fixed temperature, which most preferably is equal to the target temperature of the measurement chamber to within a few degrees Celsius, preferably to within ±1° C., to within ±0.5° C., or even to within ±0.2° C. Such an isothermal encapsulation provides a particularly stable and well-defined thermal environment for the measurement chamber set-up. This has the advantage that heat loss from the measurement chamber to the environment is minimized. This has the advantage that the heat applied by the sample heater more precisely reflects the heat required for bringing the injected liquid from the initial temperature prior to injection to the target temperature. Heat loss related artefacts are therefore reduced to a minimum, and a particularly high precision of the derived initial temperature is achieved, which furthermore is particularly robust against fluctuations in ambient temperature around the apparatus.

Advantageously according to some embodiments the initial temperature of the injected liquid is required to be in the range between 2° C. and 35° C., or between 10° C. and 33° C., or between 15° C. and 32° C. Thereby an applicable temperature range is specified, in particular for bioanalytical applications, for which a temperature measurement according to some embodiments of the invention is considered reliable, wherein a narrower initial temperature range may result in a more precise calculation of the initial temperature, whereas a wider initial temperature range allows for less restrictive specifications for the operation requirements of the apparatus.

In analogy to the heating power and flow rate, it is conceived that the skilled person may also select other parameters characterising the amount or rate of liquid injected into the sample volume and the sample heating required for setting/reaching a target temperature in the sample volume in order to determine the initial temperature of the injected liquid in an equivalent manner. For example, it is conceivable to determine the initial temperature from a volume of liquid fed to the sample volume and the corresponding integral amount of heat required for heating that amount to the target temperature.

Advantageously, the apparatus comprises at least one analyte sensor in contact with the sample volume, wherein the analyte sensor is adapted to produce an analyte sensor output based on a quantitative measurement of a quantity in respect of an analyte. Preferably, the apparatus comprises a plurality of analyte sensors in contact with the sample volume, wherein each of the plurality of analyte sensors is adapted to produce an analyte sensor output based on a quantitative measurement of a quantity of a respective analyte. Typically, the plurality of analyte sensors is for measuring a variety of different analytes.

Advantageously according to some embodiments, the apparatus further comprises at least one analyte sensor in contact with the sample volume, wherein the analyte sensor is adapted to produce an analyte sensor output representing a quantitative measure of an analyte in the liquid sample, and wherein the processor unit is further configured for correcting the analyte sensor output based on the determined initial temperature. This is particularly advantageous for measurements on liquid samples that are affected by a rapid temperature change upon injection into the measurement chamber, i.e. a change from the initial temperature of the liquid sample before injection into the measurement chamber to the target temperature to which the liquid sample is heated by the thermostatic sample heater as soon as the liquid sample enters the measurement chamber through the inlet.

Advantageously according to some embodiments, the analyte sensor output is corrected using a correction formula, wherein the correction is a function of the initial temperature of the liquid sample prior to injection into the measurement chamber. Preferably, the correction formula is stored/programmed in the processor unit. Advantageously, the correction formula is determined beforehand using calibration solutions of known/calibrated analyte content and measuring on this known calibration solutions at different temperatures (at least two different temperatures). Further advantageously, the correction formula is a polynomial, preferably a linear function. Advantageously, the coefficients of the polynomial or linear function may be determined from the correction data by means of a fitting routine, such as a least-square-fit.

Advantageously according to some embodiments, the analyte is $CO_2$. Advantageously, the analyte sensor output represents a quantitative measure of the concentration of $CO_2$ in a liquid sample. Preferably the analyte sensor output represents a quantitative measure of the partial pressure of $CO_2$ in a liquid sample, i.e. $pCO_2$. Further preferably, the liquid sample is a QC-solution for controlling the validity of $pCO_2$ measurements. Typically such a QC-solution has a calibrated $CO_2$— concentration with a $pCO_2$ value that is specified for a certain reference temperature, such as room temperature, e.g. 23° C.

A particularly pronounced example for a slow equilibrium response upon temperature changes is the $CO_2$—$(HCO_3)^-$ buffer system, due to the slow reaction between CO2 and water. The $CO_2$—$(HCO_3)^-$ buffer system is relevant for measurements of $CO_2$ concentration as the partial pressure of $CO_2$ ($pCO_2$) in a liquid sample. In most body fluids, such as blood, this reaction is accelerated by orders of magnitude, due to the presence of an enzyme, carbonic anhydrase, catalysing the reaction, and the temperature response of the equilibrium can be considered instantaneous on the time scale of minutes or even seconds. This is not the case in pure systems such as a QC-solution prepared with a specified/calibrated $pCO_2$.

In so far the $CO_2$—$(HCO_3)^-$ buffer system is also present in other reference solutions than those used for control and/or calibration of $pCO_2$ measurements, the corresponding QC and/or calibration procedures may in the same way benefit from the present invention. For example, the $CO_2$—$(HCO_3)^-$ buffer system also affects the pH-value of a solution, unless it is dominated by other buffer systems present in the solution in question. The QC and/or calibration routines for pH measurements may therefore also be subject to a slow thermal equilibrium concern, and may therefore equivalently benefit from the present invention.

In one approach, it is conceivable to achieve the same rapid equilibrium response in a QC-solution for asserting the correctness of $pCO_2$ measurements, by adding the same catalysing enzyme, carbonic anhydrase, to the QC-solution. However, this is an expensive approach, for the following reasons. QC-procedures are performed frequently. QC-solutions are therefore consumables used at a considerable amount. Carbonic anhydrase, on the other hand, has a high prize. Addition of carbonic anhydrase to the QC-solutions would therefore considerably, if not prohibitively, increase the cost for such a QC-solution, and thus the cost of running the bioanalysis apparatus—at least in the long run.

It is an important merit of the present invention to establish that simple QC-solutions without an additive, such as the catalysing enzyme carbonic anhydrase, can still be used for obtaining accurate QC-measurements for $pCO_2$ in rapid measurement cycles of the order of minutes, or even seconds, despite a much longer half time for the equilibrium response to rapid temperature changes of such simple QC-solutions. As discussed further below, this is established by showing that the errors resulting from a lagging equilibrium formation can be treated as systematic errors on the time scale of the measurement cycles involved. The apparently erroneous $pCO_2$ measurement values can therefore be assigned to appropriately corrected values using a correction formula.

Advantageously according to some embodiments, the processor unit is configured for correcting the analyte sensor output directly based on fluid flow data from the fluid handling system and sample heating data from the sample heater device. Since the initial temperature may be uniquely derived or estimated from a calibration curve, and since the analyte sensor output may be corrected based on the thus derived initial temperature using a correction formula that has been established at known temperatures, the analyte sensor output correction may be directly mapped from the fluid flow and sample heating data using an appropriate mapping function. The mapping function may e.g. be derived by combining the calibration and correction formulas, or may also be directly determined beforehand in a calibration routine for a given type of apparatus. As above, the mapping formula may be represented by any suitable function, and may be estimated, approximated or fitted using e.g. a polynomial curve, or a linear function (i.e. first order polynomial with a slope and offset as coefficients). As for the calibration formula mentioned above, the mapping formula may also take into account different fixed target temperatures. The mapping may also be stored/programmed in the processor unit in any suitable format, such as an explicit function, or a look-up table.

Advantageously according to some embodiments, the processor unit is further configured for comparing the analyte sensor output to a nominal value. Further advantageously the processor unit is further configured for comparing the analyte sensor output to a validity range with an upper limit value and a lower limit value. Advantageously, the upper and lower limits are determined by a nominal value and specified tolerances. This is particularly useful for the assessment of the validity of a measurement in the course of quality control procedures, where the nominal value is a nominal value for an analyte quantity of a QC-solution, e.g. a nominal $pCO_2$ of a QC-solution for $pCO_2$ measurements, and the specified tolerances are tolerances specified for validation in a QC-manual. The QC-manual may, e.g. be the consequence of manufacturer specifications or regulations, such as the above-mentioned Rili-BÄK for the quality control of laboratory-medical analyses.

Preferably, the comparison is performed by correcting the analyte sensor output and comparing the corrected analyte sensor output to a nominal value and/or comparing the corrected analyte sensor output to a validity range with an upper limit value and a lower limit value. In this case, the nominal value, as well as the upper and the lower tolerance limits are specified at the target temperature at which analyte measurements are performed.

Alternatively, the comparison is performed by determining the uncorrected analyte sensor output, correcting the nominal value and/or the upper and lower limit values to corresponding corrected nominal, upper limit, and lower limit values at the initial temperature that has been determined for the sample liquid, and comparing the uncorrected analyte sensor output to the corrected nominal value and/or comparing the uncorrected analyte sensor output to a corrected validity range according to the corrected upper limit and lower limit values.

Advantageously, the processor device may further provide a validation output in relation to the analyte sensor based on any of the above comparisons.

Corresponding methods for determining an initial temperature of a liquid sample prior to injection into a thermostatically controlled measurement chamber and for determining a correction of an analyte sensor output based on injection flow and sample heater data may be defined as follows. The corresponding advantages as mentioned above with respect to the apparatus are also achieved by these methods.

A second aspect of the invention relates to a method for the analysis of biological liquid samples is provided, the method comprising: injecting a liquid sample into a sample volume, the liquid sample having an initial temperature, wherein the injection flow is controlled by means of a fluid handling system; upon injection, heating the injected liquid sample to a target temperature, wherein the target temperature is controlled by means of a thermostatic sample heater device; and determining the initial temperature of the liquid sample injected into the measurement chamber based on the fluid flow data from the fluid handling system and sample heating data from the sample heater device. Advantageously, the method comprises obtaining fluid flow data from the fluid handling system and sample heating data from the sample heater device and providing said fluid flow and sample heating data at a processor unit for determining the initial temperature at the processor unit.

Advantageously according to some embodiments of the method, the fluid flow data comprises a parameter representative of the flow rate of the liquid sample injected into the sample volume, and the sample heating data comprises a parameter representative of the heating power applied by the thermostatic sample heater device to establish a target temperature in the sample volume under steady flow conditions.

Advantageously according to some embodiments, the method further comprises: bringing the liquid sample inside the sample volume in contact with at least one analyte sensor and producing an analyte sensor output, wherein the analyte sensor output is representative of a quantitative measurement in respect of a quantity of a corresponding analyte in the liquid sample;

Advantageously according to some embodiments, the method further comprises: correcting the analyte sensor output based on the determined initial temperature.

Advantageously according to some embodiments of the method, the analyte sensor output is corrected using a correction formula, wherein the correction is a function of the initial temperature of the liquid sample prior to injection into the measurement chamber. Advantageously, the correction formula is determined beforehand using calibration solutions of known/calibrated analyte content and measuring on the known calibration solutions at different temperatures, such as at least two different temperatures. Further advantageously, the correction formula is a polynomial, preferably a linear function. Advantageously, the coefficients of the polynomial or linear function may be determined from the correction data by means of a fitting routine, such as a least-square-fit.

Advantageously according to some embodiments of the method, the analyte is $CO_2$. Advantageously, the analyte sensor output represents a quantitative measure of the concentration of $CO_2$ in a liquid sample. Preferably the analyte sensor output represents a quantitative measure of the partial pressure of $CO_2$ in a liquid sample, i.e. $pCO_2$.

As already discussed above with respect to the apparatus it is conceivable to perform any of the initial temperature related corrections implicitly by correcting the analyte sensor output directly based on fluid flow data from the fluid handling system and sample heating data from the sample heater device using appropriate mapping.

According to a yet further aspect of the invention, a method of performing a quality control measurement on an apparatus for the analysis of biological liquid samples is provided in respect of $pCO_2$ measurements, the method comprising: Injecting a liquid sample of a QC-solution for controlling the validity of $pCO_2$ measurements into a sample volume, the QC-solution having an initial temperature, wherein the injection flow is controlled by means of a fluid handling system; upon injection, heating the injected QC-solution to a target temperature, wherein the target temperature is controlled by means of a thermostatic sample heater device; determining the initial temperature of the QC-solution injected into the measurement chamber based on the fluid flow data from the fluid handling system and sample heating data from the sample heater device; bringing the QC-solution inside the sample volume in contact with a $pCO_2$-sensor and producing a $pCO_2$-sensor output, wherein the $pCO_2$-sensor output is representative of a quantitative measurement in respect of $pCO_2$ in the QC-solution; correcting the $pCO_2$-sensor output based on the determined initial temperature; comparing the corrected $pCO_2$-sensor output to a nominal value for $pCO_2$ in the QC-solution and/or comparing the corrected $pCO_2$-sensor output to a validity range with an upper limit value and a lower limit value; and providing a QC-validation output in relation to the $pCO_2$-sensor based on at least one of the comparisons.

Advantageously, the upper and lower limits are determined by the nominal value and specified tolerances. The specified tolerances may be tolerances specified for validation in a QC-manual. The QC-manual may, e.g. be the consequence of manufacturer specifications or regulations, such as the above-mentioned Rili-BÄK for the quality control of laboratory-medical analyses. The determination of the temperature and/or the consequential corrections of the sensor output may be expressed in any suitable form, e.g. as formulae as discussed above. As also discussed before, the correction of the sensor output for effects related to an initial temperature below the target temperature may also be conceived to be applied implicitly using appropriate mapping.

In a yet further aspect, the present invention is also useful for providing an improved method of calibrating a device for measuring the concentration of creatinine. Methods of calibrating such a device using one or more calibration solutions are e.g. disclosed and discussed in detail in the international patent applications WO 2016/096725 A1 and WO 2016/097078 A1, which are hereby included by reference. These patent applications relate to methods of calibrating a device for measuring the concentration of creatinine using one or more calibration solutions, the method comprising: receiving concentrations at an initial time of creatine, Cr, and/or creatinine, Cm, of the one or more calibration solutions; receiving outputs of the measuring device at the end time; calculating the concentration of Cr and/or Cm in the calibration solutions at an end time using a temperature model, wherein the temperature model indicates changes in temperature of the calibration solutions from the initial time to the end time; and determining a relationship between the outputs of the measuring device and the calculated concentrations of Cr and/or Crn. The methods are e.g. defined in the independent claims of the above-mentioned international patent applications WO 2016/096725 A1 and WO 2016/097078 A1, wherein further advantageous methods are e.g. disclosed in the corresponding dependent claims.

Advantageously according to some embodiments of the invention, these methods of calibrating a device for measuring the concentration of creatinine using one or more calibration solutions may e.g. be improved by taking into account continued changes in the actual temperature of the one or more calibration solutions as tracked by the temperature estimation technique according to embodiments of the present invention. The temperature may be tracked using continued estimation of the initial temperature of the one or more calibration solution by means of the present invention, e.g. each time a calibration using these calibration solutions is performed, such as several times a day, or at least once a day, or at least once every other day. Thereby a more accurate estimation of the temperature history is tracked and can be used for more precisely and in a simple manner determining an actual state of the one or more calibration solution packs. Furthermore, the improvement of the calibration method is suited for retro-fitting existing apparatus in a similar way as discussed above.

By the embodiments according to the invention as disclose herein, a measurement apparatus and method is provided allowing for continued correction of temperature related errors in a user friendly manner. The correction explicitly or implicitly takes into account the actual initial temperature of the liquid immediately before injection of the liquid sample into the measurement chamber, and thus may account for the thermal history of the liquid sample, and in particular for the temperature step the liquid sample experiences upon injection into the thermostatically controlled measurement chamber. The temperature estimation and consequential correction may be performed in an automated manner and is suited for retro-fit modification of existing apparatus without the need for significant hardware adaptations. The apparatus may thus be adapted to communicate/retrieve flow and heater data to the processor unit, which then determines the initial temperature of the liquid sample and/or a correction of analyte sensor output based on this data. By the apparatus according to some embodiments of the invention, it can thus be avoided to require a user to estimate and enter a temperature value for the initial temperature. Further according to some embodiments of the invention, the problem of an expensive hardware modification for acquiring reliable temperature information can be overcome.

BRIEF DESCRIPTION OF THE DRAWINGS

Preferred embodiments of the invention will be described in more detail in connection with the appended drawings, which show in FIG. 1 schematically an apparatus for the analysis of biological liquid samples according to one embodiment of the invention, FIG. 2 a graph of a temperature calibration relation averaged over a group of biomedical analysis instruments of the type used for the $pCO_2$ measurements in the examples, FIG. 3 for one of the instruments of FIG. 2, a parameter representative of the heating applied by the thermostatic sample heater to a liquid injected at two different flow rates, and in FIGS. 4a-4c the analyte sensor output at different initial temperatures for three different liquid samples as obtained from one of the instruments of FIG. 2.

DETAILED DESCRIPTION

Figure 1:
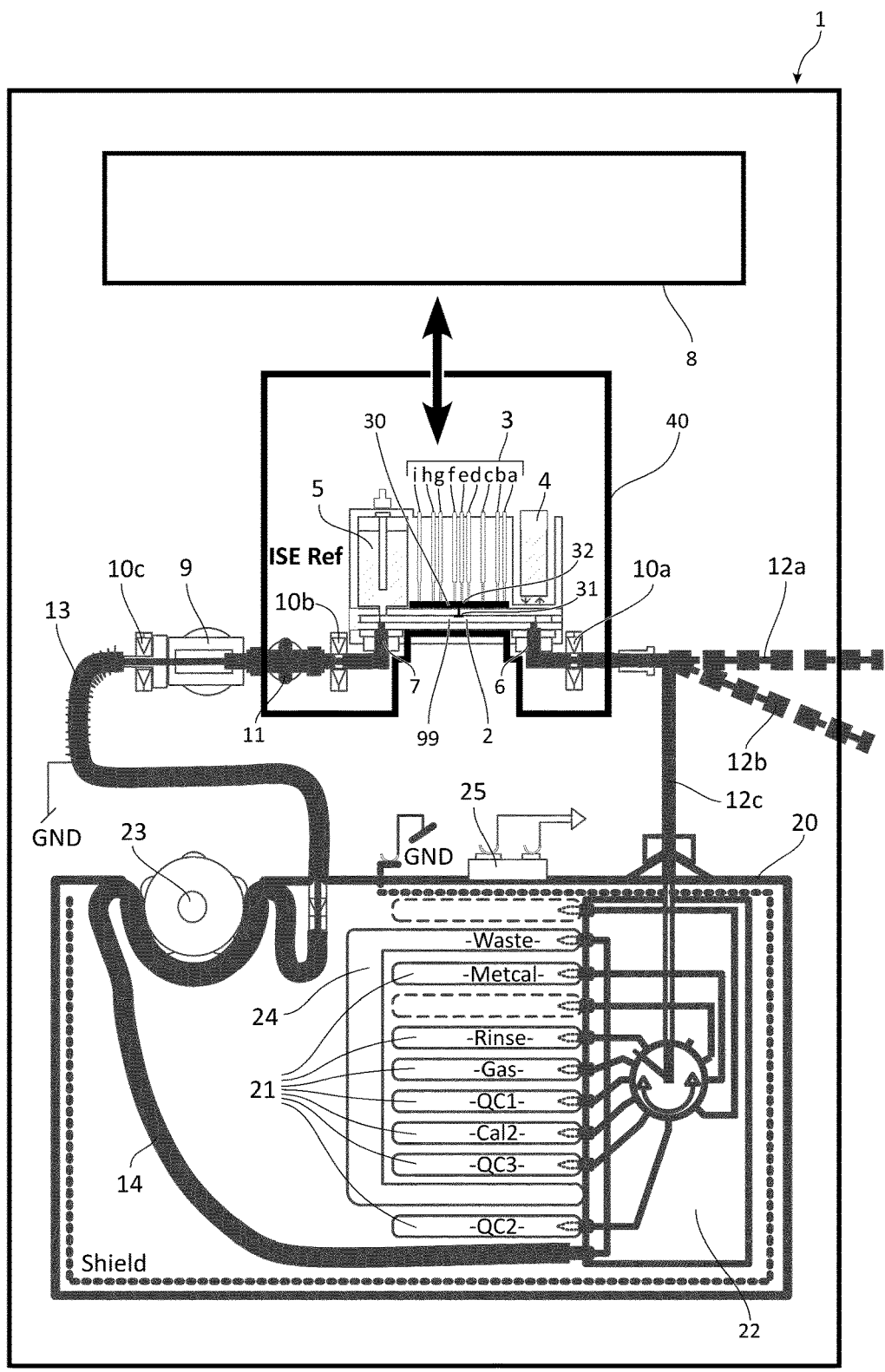

FIG. 1 shows schematically an apparatus 1 for the analysis of biological liquid samples, such as body fluids. The apparatus 1 has an analyser assembly with a measurement chamber 2, which is equipped with one or more analyte sensors 3(a-i), 4, and a reference electrode 5. The apparatus 1 further comprises a fluid handling system 20 adapted for feeding a liquid sample to the sample volume through an inlet 6 of the measurement chamber and for removing the liquid sample through an outlet 7 of the measurement chamber 2. The apparatus 1 has a thermostatic sample heater device 30 adapted for controlling a sample temperature of the liquid sample in the measurement chamber 2. The sample heater device 30 has a temperature sensor 31, here a thermistor, which is arranged on an inside surface of the measurement chamber 2 half way between the inlet 6 and the outlet 7, a temperature controller (not shown), and a resistive sample heating element 32 arranged in good thermal contact with the measurement chamber on the rear side of a substrate forming a top wall of the measurement chamber 2. The temperature sensor 31 is for measuring the temperature of a liquid sample inside the measurement chamber, and providing the measurement result to the temperature controller. The temperature controller operates the sample heater 32 in response to the temperature reading to bring the temperature in agreement with a target temperature where measurements are to be performed. The apparatus 1 has furthermore a processor unit 8, which is adapted to receive flow data from the fluid handling system 20 and sample heating data from the thermostatic sample heater device 30. The processor unit 8 comprises programmed instructions for determining an initial temperature of the liquid sample injected into the measurement chamber 2 based on the flow data from the fluid handling system 20 and the sample heating data from the thermostatic sample heater device 30.

For performing measurements, a user may provide a liquid sample at an input port 12a/b of the apparatus 1. The liquid sample is transferred through an inlet 6 to the measurement chamber 2 comprising a plurality of analyte sensors 3, 4. The analyte sensors 3, 4 are arranged to provide essentially simultaneous measurements on analyte parameters in a liquid sample, e.g. a whole blood sample. Preferably, the required sample amount for obtaining precise and reliable analysis data is as small as possible. A detailed example of a sensor assembly design that is particularly suitable for simultaneously measuring a plurality of different parameters in bodily fluids, particularly in whole blood, and its use in a blood analyser is e.g. found in EP 2 147 307 B1 or the above-mentioned U.S. Pat. No. 8,728,288 B2. Following pre-programmed instructions loaded in a processor unit 8 and/or user input, measurements are performed using the analyte sensors 3, 4. The analyte sensors 3, 4 generate quantitative signals that are representative of a physical parameter for the respective analyte and provide the signals to the processor unit 8. The processor unit 8 is adapted to receive and process signals from the analyte sensors 3, 4, and present the processed signals as output to a user and/or to a subsequent/further data analysis. After measurement, the liquid sample is discharged, and the measurement chamber 2 is prepared for the next measurement. The embodiment of the apparatus 1 shown in FIG. 1 is particularly adapted for the measurement of blood parameters, and further comprises an optional oxygenation measurement device 9 downstream of the measurement chamber 2. Performing the measurements, calibration tasks, and quality control procedures thus typically involves the loading, unloading, rinsing, cleaning and re-loading of different liquids, which may be done using the infrastructure of the fluid handling system 20. The fluid handling may be controlled in an automated way by the processor unit 8 according to pre-programmed instructions and/or user input. The fluid handling system 20 includes a number of reservoirs 21 pre-filled with process liquids (here denoted RINSE/CAL1, CAL2, QC1, QC2, QC3) for rinsing/wash-out, calibration and quality control tasks. The process liquids (RINSE/CAL1, CAL2, QC1, QC2, QC3) have a known composition. The exact composition of a given batch may be stored in a chip 25 that may be attached to a cassette comprising the reservoirs 21, wherein the chip 25 may be read by the processor unit 8. The process liquid (RINSE/CAL1, CAL2, QC1, QC2, QC3) for a given process step may be selected by a fluid selector valve 22, and via feed line 12c transferred through the inlet 6 to the measurement chamber 2. Correct filling of the measurement chamber 2 may be monitored and verified by visual inspection or according to known procedures by observing the propagation of a liquid interface through the system by means of liquid sensors 10a, 10b, 10c located upstream and downstream of the measurement chamber, such as at the inlet 6 (liquid sensor 10a), at the outlet 7 (liquid sensor 10b), and just after the oxygenation measurement device 9 (liquid sensor 10c), respectively. The fluid flow through the apparatus 1 is driven by a pump 23, here a peristaltic hose-pump arranged downstream of the measurement chamber 2 and the oxygenation measurement device 9 and connected thereto via fluid line 13. The discharged fluids are finally transported through fluid line 14 to the waste reservoir 24.

Upon start-up and, in an ongoing manner, during uptime, the apparatus 1 performs self-control routines including QC measurements. If any abnormality is detected, the apparatus 1 indicates the deviation to a user, and may further indicate ways of overcoming an error state. On the other hand, when the apparatus 1 indicates normal operation, measurements can be performed immediately. Advantageously according to some embodiments, the self-control routines may be performed during idle times, i.e. when the apparatus 1 is in an idle state, where it is not used for performing actual measurements on a user's sample. The self-control control routines may include continued quality control measurements performed on suitable QC-solutions provided in so-called solution packs. The QC-solution packs may be replaceably installed in the apparatus. A QC-solution may also be provided to the apparatus from an external source through an inlet port, such as sample ports 12a, 12b. The QC-solutions have a precisely known composition, which is specified by the manufacturer and e.g. stored on chip 25. Where relevant, the specification of a nominal concentration may be given for a certain equilibrium temperature, such as at 23° C. Corresponding values for the nominal concentration at different equilibrium temperatures may be assigned according to respective assignment tables or curves.

The analyser assembly of apparatus 1 is furthermore encapsulated by a thermostatic encapsulation 40. The walls of the thermostatic encapsulation 40 form a housing with walls held at a fixed temperature. The thermostatic encapsulation 40 thus acts as a thermal shield to the analyser assembly maintaining the immediate environment of the measurement chamber at the fixed temperature of the encapsulation 40. Most preferably, the fixed temperature of the thermostatic encapsulation 40 is set to the target temperature.

EXAMPLE

Figure 2:
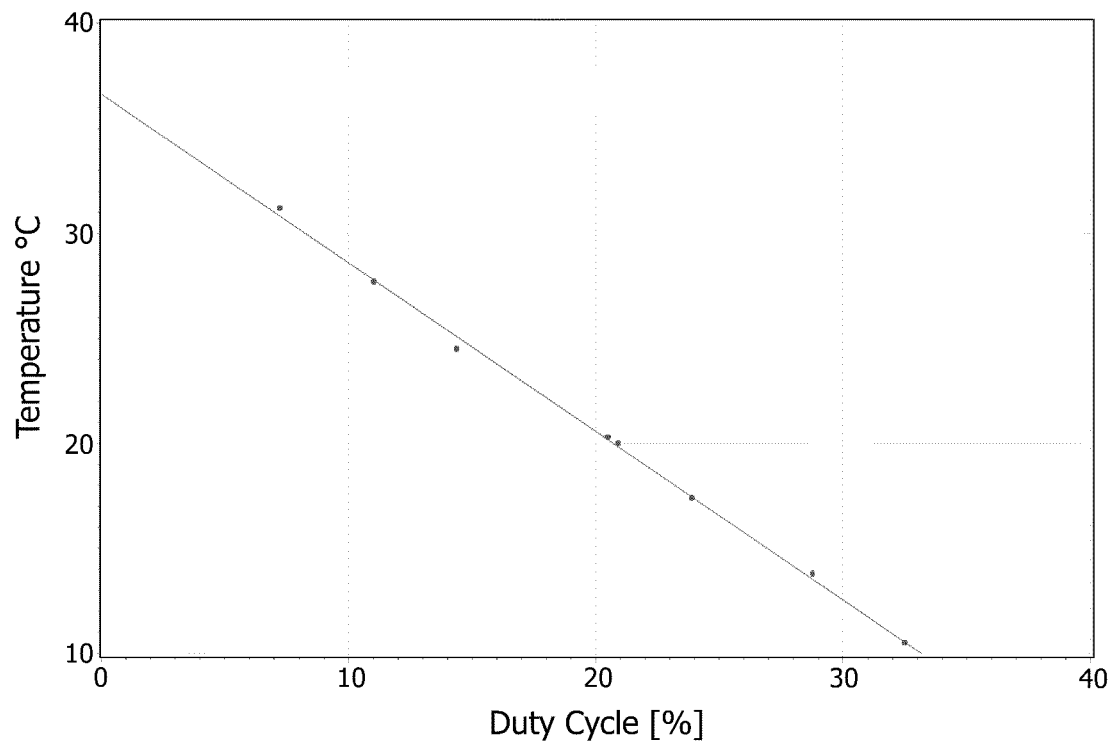
Figure 3:
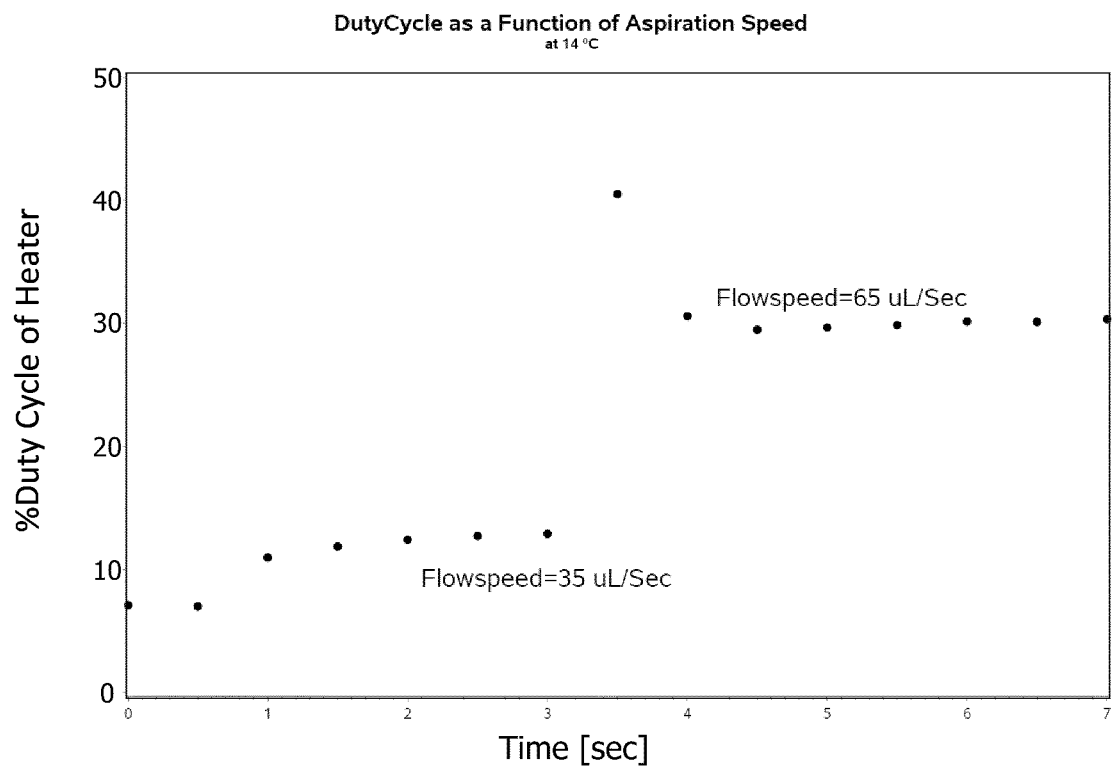

Referring to FIGS. 2-4 in the following, an example for determining the temperature calibration and for correcting an analyte sensor output for $pCO_2$ sensors is given, which is useful for eliminating the influence of temperature effects on QC-measurements. The calibration and correction relations derived below are valid for a given type of apparatus, and can accordingly be provided in the software of all instruments of the same apparatus type.

FIG. 2 shows an example of a temperature calibration obtained on a group of ten analyser instruments of the same apparatus type, ABL90 available from Radiometer Denmark. A schematic of the apparatus type is given in FIG. 1. The ten individual instruments were placed in a climate test room allowing to precisely controlling a room temperature in the range between 10° C. and 32° C. At a given room temperature, the instruments were allowed to settle. With the instruments in thermal equilibrium at a given room temperature, a series of QC-measurements where performed, injecting a liquid sample of a QC-solution through the inlet into the measurement chamber by aspiration from the outlet by a pump, i.e. by applying suction from the downstream end of the measurement chamber. The injection was performed at a fixed flow rate of 65 µl/s (microliters per second) as controlled by the flow handling system. Prior to injection, the liquid sample has the same temperature as the room temperature. Upon injection, the liquid sample is then heated to a target temperature by the thermostatic sample heater device. The target temperature was set to 37° C. for all experiments. The analyser assembly of the apparatus type used is encapsulated by a thermostatic encapsulation, which for all experiments also was set to the same temperature as the target temperature of the measurement chamber, i.e. to 37° C. Thereby a particularly well-controlled thermal behaviour is achieved for the measurement chamber as discussed above. A parameter representative of the heating power applied by the sample heater device is then retrieved from the sample heater device. The sample heater device of the above apparatus type is configured to control the heating power applied by varying a duty cycle of a heater current applied to an electric heater in respect of a difference between the target temperature and an actual sample temperature as measured by a temperature sensor arranged in the measurement chamber. The duty cycle data may thus be used as a parameter that is representative of the heating power applied by the thermostatic sample heater device in order to bring the liquid sample injected at room temperature with the given flow rate of 65 µl/s to the target temperature. The same experiment was repeated for each instrument at a number of different room temperature settings. In the graph shown in FIG. 2, the room temperature, corresponding to the initial temperature of the liquid sample, is plotted against the corresponding duty cycle readings of the thermostatic heater device averaged over all ten instruments. The obtained relationship may be used as a calibration curve for determining the initial temperature of an injected sample. The solid line in FIG. 2 is a straight line least square fit and provides a calibration curve for estimating the initial temperature in degrees Celsius from the duty cycle reading in percent taken at an injection flow rate setting of 65 µl/s as:

$$T(\text{initial})/°C = -0.8 \times (\text{duty cycle}/\%) + 36.6;$$

The temperature calibration curve of FIG. 2 is valid for instruments of the same type and for a fixed flow rate setting of 65 µl/s chosen for the experiments. Here, the flow data obtained from the fluid handling system is the flow rate setting. Potential instrument-specific variations in the temperature calibration may be determined and may be compensated accordingly by an instrument specific temperature calibration, if such variations are considered significant. For example, variations in the resistance of the electrical heater elements of different instruments may be compensated by applying a scaling factor to the duty cycle reading, which is proportional to the deviation of the instrument-specific heater element resistance from a nominal heater element resistance.

FIG. 3 shows from the same series of experiments as the data of FIG. 2 a time series of duty cycle readings, wherein a first set of duty cycle readings was obtained for an injection flow rate setting of 35 µl/s and wherein, after a step change in flow rate setting, a second set of duty cycle readings was obtained for an injection flow rate setting of 65 µl/s. All duty cycle readings have been obtained for the same initial temperature as determined by the room temperature of 14° C., and on the same instrument. The graph of FIG. 3 illustrates the injection flow rate dependency of the heating power applied by the thermostatic sample heater in order to bring the injected liquid sample from its initial temperature to the target temperature of 37° C.

Figure 4A:
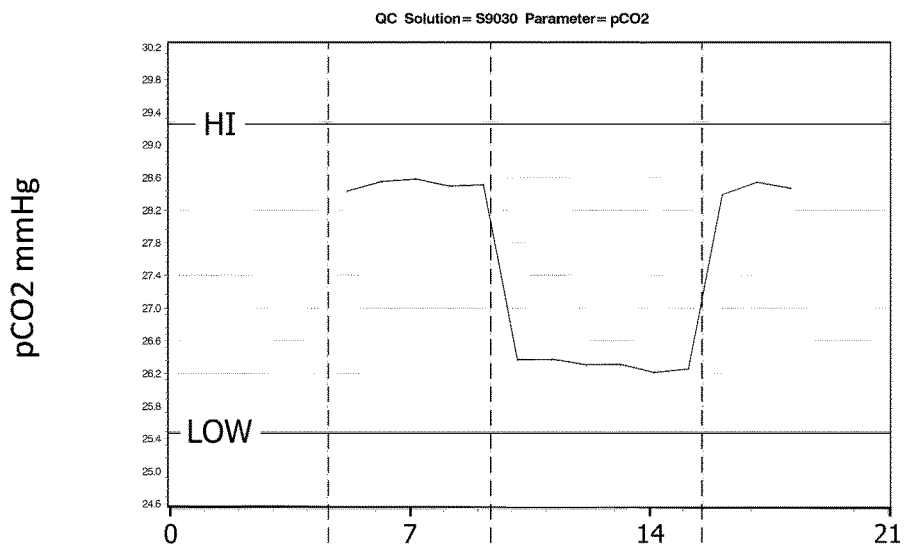
Figure 4B:
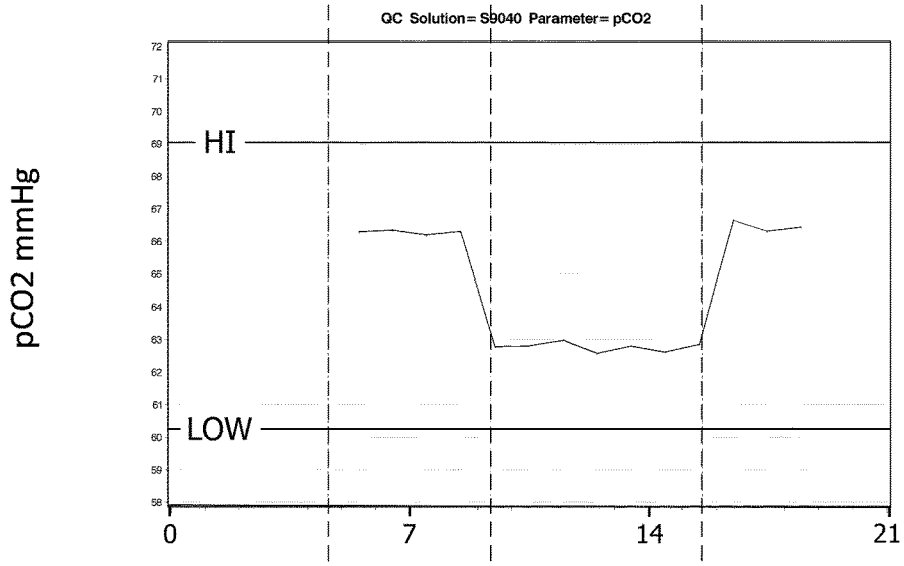
Figure 4C:
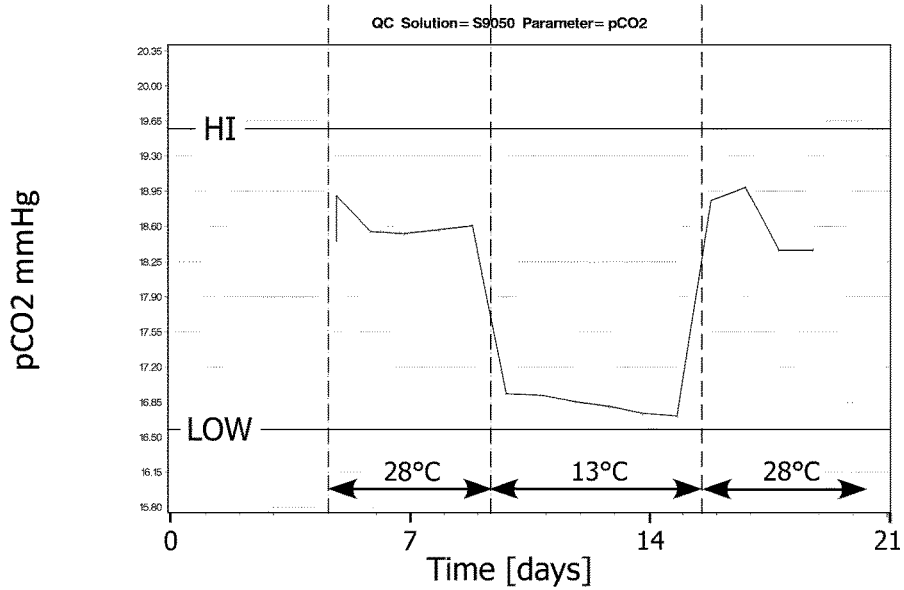

FIG. 4a-c from the same series of experiments as the data of FIGS. 2 and 3 a composite plot with three series of $pCO_2$ measurements taken on three different QC-solutions of known composition: S9030 with a nominal value for $pCO_2$ of 30 mm Hg at 23° C. (FIG. 4a); S9040 with a nominal value for $pCO_2$ of 67 mm Hg at 23° C. (FIG. 4b); and S9050 with a nominal value for $pCO_2$ of 20 mm Hg at 23° C. (FIG. 4c).

The $pCO_2$ measurements were taken at two different room temperatures over a span of several days, first maintaining a room temperature of 28° C., then reducing the room temperature to 13° C., and finally returning back to a room temperature of 28° C. The $pCO_2$ measurements were all performed using the same protocol, including timing, of filling the measurement chamber with a liquid sample, pre-heating the liquid sample during the filling procedure to the target temperature using the thermostatic sample heater device, and as soon as the target temperature was achieved, switching off the thermostatic sample heater device and obtain a $pCO_2$ sensor output reading. The obtained $pCO_2$ sensor output reading is plotted in the graphs together with respective upper limits, marked "HI", and lower limits, marked "LOW", for each of the three QC-solutions. The upper and lower limits (HI, LOW) are determined with respect to the nominal value for the $pCO_2$ of the respective QC-solution, in agreement with the RiLi-BÄK guidelines of 19 Sep. 2014.

Table 1 lists nominal compositions of the three QC-solutions. While the respective nominal values may be taken from such a table, the actual composition may slightly deviate from these tabulated values within production tolerances. The actual analyte composition for each solution in a solution pack lot is therefore typically included in a smart chip contained in each solution pack. The actual values for the nominal concentrations may thus be read into the processor unit when the solution pack is installed in an instrument. This allows for even better precision in the QC-procedure. The upper and lower limits (HI, LOW) shown in the FIGS. 4a-c have been determined using the above-mentioned Rili-BÄK guidelines based on the actual values for the nominal pCO2 of the respective QC-solutions (S9030, S9040, S9050).

TABLE 1

Composition table with nominal pCO2 values at 23° C. for QC-solutions S9030, S9040, and S9050

| | | Concentration | | | |
|---|---|---|---|---|---|
| | | S9030 | S9040 | | S9050 |
| | | | (QC 2) | | |
| Substance | Unit | (QC 1) Solution | Solution | Gas pO$_2$ (at 760 mmHg) | (QC 3) Solution |
| pH | | 7.2 | 6.8 | NA | 7.5 |
| pCO$_2$ | mmHg | 30 | 67 | NA | 20 |
| pO$_2$ | mmHg | 180 | | 300 (42.07%) | 20 |
| cNa$^+$ | mmol/L | 140 | 118 | NA | 175 |
| cK$^-$ | mmol/L | 4 | 7 | NA | 1.8 |
| cCl$^-$ | mmol/L | 105 | 95 | NA | 125 |
| cCa$^{2-}$ | mmol/L | 0.8 | 1.65 | NA | 0.3 |
| cGlu | mmol/L | 0 | 15 | NA | 7 |
| cLac | mmol/L | 0 | 8 | NA | 4 |
| ctBil* | µmol/L | 0 | 300 | NA | 450 |
| ctHb | mmol/L | 0 | 8 | NA | 12 |
| SO$_2$ | % | | 97 | NA | 70 |
| FO$_2$Hb | % | | 92 | NA | 49 |
| FCOHb | % | | 3 | NA | 20 |
| FMetHb | % | | 2 | NA | 10 |
| FHbF | % | | 80 | NA | 50 |

From all three graphs, FIGS. 4a-c a clearly systematic temperature dependence of the analyte sensor output is evident. Furthermore, a correction curve may be determined for the $pCO_2$ measurement for each of the QC-solutions (S9030, S9040, S9050) as a linear fit to the $pCO_2$ measurement as a function of temperature:

$$S9030: pCO_2(T)/\text{mm Hg} = (pCO_2/\text{mm Hg}) + 0.145 \times (23-(T/° C.));$$

$$S9040: pCO_2(T)/\text{mm Hg} = (pCO_2/\text{mm Hg}) + 0.223 \times (23-(T/° C.));$$

$$S9050: pCO_2(T)/\text{mm Hg} = (pCO_2/\text{mm Hg}) + 0.115 \times (23-(T/° C.));$$

wherein $pCO_2$ refers to the uncorrected $pCO_2$ sensor output, and $pCO_2(T)$ refers to the corrected $pCO_2$-sensor output. In order to eliminate the above documented temperature effects from the quality control of the $pCO_2$ measurements, the corrected $pCO_2$ sensor output values may then be compared to the nominal upper and lower limits (HI, LOW).

The invention claimed is:

1. An apparatus comprising:
   a measurement chamber defining a sample volume with an inlet and an outlet;
   a fluid handling system adapted for feeding a liquid sample to the measurement chamber through the inlet and for removing the liquid sample through the outlet;
   a thermostatic sample heater device that controls a sample temperature of the liquid sample in the measurement chamber; and
   a processor unit; wherein the processor unit determines an initial temperature of the liquid sample injected into the measurement chamber based on flow data from the fluid handling system and sample heating data from the sample heater device.

2. The apparatus according to claim 1, wherein the flow data comprises a parameter representative of a flow rate of the liquid injected to the measurement chamber, and the sample heating data comprises a parameter representative of a heating power applied by the thermostatic sample heater device to establish a target temperature in the measurement chamber under steady flow conditions.

3. The apparatus according to claim 1, wherein the thermostatic sample heater device regulates a sample temperature of the liquid sample in the measurement chamber according to a target temperature setting.

4. The apparatus according to claim 1, wherein the thermostatic sample heater device comprises an electric heating element physically attached to or integrated with walls of the measurement chamber.

5. The apparatus according to claim 1, wherein a target temperature in the measurement chamber is in a range between 35° C. and 39° C.

6. The apparatus according to claim 1, wherein the apparatus comprises an isothermal encapsulation of the measurement chamber, wherein the isothermal encapsulation encloses the measurement chamber with thermally controlled and/or thermally regulated inner surfaces.

7. The apparatus according to claim 6, wherein the temperature of the inner surfaces of the isothermal encapsulation is controlled and/or regulated to a fixed temperature.

8. The apparatus according to claim 1, wherein the measurement chamber is equipped with at least one analyte sensor in contact with the liquid sample, wherein the at least one analyte sensor is adapted to produce an analyte sensor output representing a quantitative measurement of an analyte in the liquid sample.

9. The apparatus according to claim 8, wherein the processor unit is further configured for correcting the analyte sensor output based on the determined initial temperature.

10. The apparatus according to claim 8, wherein the analyte is $CO_2$.

11. The apparatus according to claim 8, wherein the analyte sensor output represents a quantitative measure of a partial pressure of $CO_2$, $pCO_2$, in the liquid sample.

12. The apparatus according to claim 8, wherein the processor unit is further configured for comparing the analyte sensor output to a nominal value and/or wherein the processor unit is configured for comparing the analyte sensor output to a validity range with an upper limit value and a lower limit value.

13. The apparatus according to claim 12, wherein the processor unit further provides a validation output in relation to the at least one analyte sensor based on the comparison.

14. A method comprising:
bringing the liquid sample into a measurement chamber, the liquid sample having an initial temperature, wherein an injection flow is controlled by means of a fluid handling system;
upon injection, heating the injected liquid sample to a target temperature by means of a thermostatic sample heater device; and
determining the initial temperature of the liquid sample injected into the measurement chamber based on fluid flow data from the fluid handling system and sample heating data from the sample heater device.

15. The method according to claim 14, wherein the fluid flow data comprises a parameter representative of a flow rate of the liquid sample injected into the measurement chamber, and the sample heating data comprises a parameter representative of a heating power applied by the thermostatic sample heater device to establish a target temperature in the measurement chamber under steady flow conditions.

16. The method according to claim 14, the method further comprising:
bringing the liquid sample inside the measurement chamber in contact with at least one analyte sensor and producing an analyte sensor output, wherein the analyte sensor output is representative of a quantitative measurement in respect of a quantity of a corresponding analyte in the liquid sample.

17. The method according to claim 16, the method further comprising:
correcting the analyte sensor output based on the determined initial temperature.

18. The method according to claim 17, wherein the analyte sensor output is corrected using a correction formula, wherein the correction formula is determined beforehand using solutions of known/calibrated analyte content and measuring the known solutions at different temperatures.

19. The method according to claim 17, wherein the analyte sensor output is corrected using a correction formula, wherein the correction formula is a polynomial.

20. A method of performing a quality control measurement in respect of $pCO_2$ measurements in an apparatus for the analysis of biological liquid samples, the method comprising:
injecting a liquid sample of a QC-solution for controlling a validity of $pCO_2$ measurements into a sample volume, the QC-solution having an initial temperature, wherein an injection flow is controlled by means of a fluid handling system;
upon injection, heating the injected QC-solution to a target temperature by means of a thermostatic sample heater device;
determining the initial temperature of the QC-solution injected into a measurement chamber based on fluid flow data from the fluid handling system and sample heating data from the sample heater device;
bringing the QC-solution inside the sample volume in contact with a $pCO_2$-sensor and producing a $pCO_2$-sensor output, wherein the $pCO_2$-sensor output is representative of a quantitative measurement in respect of $pCO_2$ in the QC-solution;
correcting the $pCO_2$-sensor output based on the determined initial temperature to obtain a corrected $pCO_2$-sensor output, and comparing the corrected $pCO_2$-sensor output to a nominal value for $pCO_2$ in the QC-solution and/or comparing the corrected $pCO_2$-sensor output to a validity range with an upper limit value and a lower limit value; or
correcting a nominal value for $pCO_2$ in the QC-solution based on the determined initial temperature to obtain a corrected nominal value for $pCO_2$ in the QC-solution and/or correcting an upper limit value and a lower limit value based on the determined initial temperature to obtain corrected upper and lower limit values, and comparing the $pCO_2$-sensor output to the corrected nominal value for $pCO_2$ in the QC-solution and/or comparing the $pCO_2$-sensor output to a corrected validity range with the corrected upper and lower limit values; and
providing a QC-validation output in relation to the $pCO_2$-sensor based on the comparison.

* * * * *